US008907082B2

(12) United States Patent
Hage et al.

(10) Patent No.: US 8,907,082 B2
(45) Date of Patent: Dec. 9, 2014

(54) 1,2-BIS-(4,7-DIMETHYL-1,4,7-TRIAZA CYCLONON-1-YL)-ETHANE AND INTERMEDIATE FOR THE SYNTHESIS OF SAME

(75) Inventors: Ronald Hage, Leiden (NL); Jean Hypolites Koek, Vlaardingen (NL); Stephen William Russell, Rhoon (NL); Lodewijk Van der Wolf, Vlaardingen (NL); Jianrong Zhang, Shanghai (CN); Wei Zhao, Shanghai (CN); Xiaohong Wang, Shanghai (CN)

(73) Assignee: Catexel Limited, London (GB)

(*) Notice: Subject to any disclaimer, the term of this patent is extended or adjusted under 35 U.S.C. 154(b) by 11 days.

(21) Appl. No.: 13/808,565

(22) PCT Filed: Jul. 5, 2011

(86) PCT No.: PCT/CN2011/001104
§ 371 (c)(1),
(2), (4) Date: Jun. 21, 2013

(87) PCT Pub. No.: WO2012/003712
PCT Pub. Date: Jan. 12, 2012

(65) Prior Publication Data
US 2013/0261297 A1    Oct. 3, 2013

(30) Foreign Application Priority Data

Jul. 6, 2010  (WO) ............... PCT/CN2010/001007
Jul. 6, 2010  (WO) ............... PCT/CN2010/001008

(51) Int. Cl.
C07D 255/02    (2006.01)
C07D 403/06    (2006.01)
(52) U.S. Cl.
CPC ............ C07D 255/02 (2013.01); C07D 403/06 (2013.01)
USPC ........................................ 540/474
(58) Field of Classification Search
CPC ................... C07D 255/02; C07D 403/06
See application file for complete search history.

(56) References Cited

U.S. PATENT DOCUMENTS 5,284,944 A    2/1994  Madison et al.
2005/0112066 A1    5/2005  Winchell

FOREIGN PATENT DOCUMENTS

WO    WO 2006/125517 A1    11/2006
WO    WO 2012/107717 A1    8/2012

OTHER PUBLICATIONS

Lazar, I., et al. "Convenient Synthesis of Mono- and Ditosylated 1,4,7-triazacyclononane." Synthetic Communications. (2001), 31(20), pp. 3141-3144.*

Clark, J., et al. "The Reactions of Acid Anhydrides With Ammonia and Primary Amines." (C) 2004. Available from: < http://www.chemguide.co.uk/organicprops/anhydrides/nitrogen.html#top >.*
"Table of Strong Acids." (C) Dec. 6, 2007. Available from: < http://web.archive.org/web/20071206021945/http://www.chemistry.pomona.edu/Chemistry/1alab/www/fall2006/powerptpresentations/5Anions/acidbaseT.htm >.*
Wieghardt, K., et al. "Coordination Chemistry of the Bimacrocylic, Potentially Binucleating Ligand . . . . " Inorg. Chem. (1985), vol. 24, pp. 1230-1235.*
Hanke, D., et al. "Synthesis and X-ray and Neutron Structures of anti-[L2Rh2(H)2(μ-H)2](PF6)2 (L=1,4,7-Trimethy1-1,4,7-triazacyclononane) and a Related Species Containing a syn-[Rh2(H)2(μ-H)2]2+ Core. Isolation of [L2Fe2(μ-H)3]BPh4." Inorg. Chem. (1993), vol. 32, pp. 4300-4305.*
Balogh E. et al., "Dinuclear Complexes Formed with the Triazacyclononane Derivative ENOTA4-: High-Pressure 170 NMR Evidence of an Associative Water Exchange on [MnII2(ENOTA)(H20)2]", Inorg. Chem., 46(1), 238-250 (2007).
Blake A J et al., "Synthesis and characterisation of pendant-arm amino derivatives of 1,4,7-triazacyclononane and alkyl-bridged bis(1,4,7-triazacyclononane) macrocycles and complexation to Cu(II)", J. Chem. Soc., Dalton Trans., 3034-3040 (2000).
Brudnell S J et al., "Binuclear Copper(II) Complexes of Bis(pentadentate) Ligands Derived from Alkyl-Bridged Bis(1,4,7-triazacyclonane) Macrocycles", Inorg. Chem., 35(7), 1974-1979 (1996).
Brudnell S J et al., "Structural, EPR, and Electrochemical Studies of Binuclear Copper(II) Complexes of Bis(pentadentate) Ligands Derived from Bis(1,4,7-triazacyclonane) Macrocycles", Inorg. Chem., 37(15), 3705-3713 (1998).

(Continued)

*Primary Examiner* — Noble Jarrell
*Assistant Examiner* — John S Kenyon
(74) *Attorney, Agent, or Firm* — Knobbe, Martens, Olson & Bear, LLP

(57) ABSTRACT

The present invention provides improved processes for the synthesis of 1,4-ditosyl-1,4,7-triazacyclonone, comprising deprotecting a compound of formula (C):

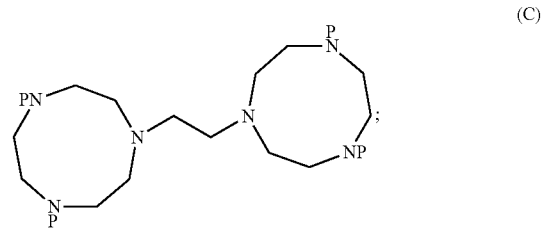

wherein P is tosylate or arylsulfonate, with an acidic medium to form 1,2-bis(1,4,7-triazacyclonon-1-yl)-ethane; and subsequently adding formaldehyde and formic acid to the acidic medium to form 1,2-bis-(4,7-dimethyl-1,4,7-triazacyclonon-1-yl)-ethane (Me$_4$-DTNE). The syntheses of intermediates are also disclosed.

22 Claims, No Drawings

(56) References Cited

OTHER PUBLICATIONS

Geilenkirchen A. et al., "Synthesis, Properties and Crystal Structures of [RuIII2(tacn)2(fJ.-OH)2(fJ.-CO3)] Br2O3.15H20 and [Ru3.52(dtne) (fJ.-O )2(fJ.-CO3)] PF6"5H20[tacn=1,4,7-triazacyclononane, dtne1,2-bis(1,4,7-triazacyclononan-l-yl)ethane] t", *J. Chem. Soc., Dalton Trans.*, 457-464 (1994).

Haidar R. et al., "Copper(II) Complexes of Bis(1,4,7-triazacyclononane) Ligands with Polymethylene Bridging Groups: An Equilibrium and Structural Study", *Inorg. Chem.*, 36(14), 3125-3132 (1997).

Hanke D. et al., "Synthesis and X-ray and Neutron Structures of anf&[LzRh2(H)2(p-H)z](PF& (L=1,4,7-Trimethyl-1,4,7-triazacyclononane)a nd a Related Species Containing a syn-[Rh2(H)z(p-H)2]2+Core. Isolation of [ L2 Fe2(u-H)3]BPh4", *Inorg. Chem.*, 32(20), 4300-4305 (1993).

Jackson W G et al., "Synthesis, Structure, and Kinetics and Stereochemistry of Base-Catalyzed Hydrolysis of meso- and rac-[Co2(tmpdtne)Cl2]4+, Bis(pentaamine) Complexes Devoid of Deprotonatable NH Centers", *Inorg. Chem.*, 44(2), 401-409 (2005).

Lazar I. et al., "Convenient Synthesis of Mono- and Ditosylated 1,4,7-Triazacyclononane", *Synthetic Communications*, 31(20), 3141-3144 (2001).

Nair B U and Weyhermuller T , "Preparation and Structure of a Dinuclear Iron(III) Complex with Six terminally Coordinated Azides: A Precursor for Multidimensional Networkl", *Chemistry Letters*, 416-417 (2000).

Pulacchini S et al., "A Remarkably Efficient and Direct Route for the Synthesis of Binucleating 1,4,7-Triazacyclononane Ligands", *Synthesis*, 16, 2381-2383 (2001).

Schafer K-O et al., "Electronic Structure of Antiferromagnetically Coupled Dinuclear Manganese (MnIIIMnIV) Complexes Studied by Magnetic Resonance Techniques", *J. Am. Chem. Soc.*, 120 (50) 13104-13120 (1998).

Shastri K. , Green Chem., "Investigations into the efficacy of methyhlphosphonic acid functionalised 1,4,7-triazacyclononane ligands in bleaching catalysis", 9, 996-1007 (2007).

Sessler J L et al., "Model Studies Related to Hemerythrin. Synthesis and Characterization of a Bridged Tetranuclear Iron( 111) Complex", *Inorg. Chem.*, 29(10), 4143-4146 (1990).

Weisman G R et al., "Selective N-Protection of Medium-ring Triamines", *J. Chem. Soc., Chem. Commun.*, 886-887 (1987).

Wieghardt K. et al., "Coordination Chemistry of the Bimacrocyclic, Potentially Binucleating Ligand 1,2-Bis( 1,4,7-triaza-1-cyclononyl)ethane (dtne). Electrochemistry of Its First Transition Series Metal(I1,III) Complexes. Characterization of the New Hemerythrin Model Complex [Fez( dtne) ( p—0 ) (p-CH3CO2)Br2*H20", *Inorg. Chem.*, 24, 1230-1235 (1985).

International Search Report and Written Opinion re International Application No. PCT/CN2011/001104 Mailed on Oct. 20, 2011 in 16 pages.

International Search Report and Written Opinion re International Application No. PCT/CN2010/001008 Mailed on Apr. 28, 2011 in 14 pages.

International Search Report and Written Opinion re International Application No. PCT/CN2010/001007 Mailed on Apr. 14, 2011 in 15 pages.

\* cited by examiner

1,2-BIS-(4,7-DIMETHYL-1,4,7-TRIAZA CYCLONON-1-YL)-ETHANE AND INTERMEDIATE FOR THE SYNTHESIS OF SAME

FIELD

The present invention concerns the synthesis of an intermediate useful for the synthesis of 1,2-bis(1,4,7-triazacyclonon-1-yl)-ethane ($Me_4$-DTNE); and the synthesis of binucleating macrocyclic ligands that may be used to form complexes that have utility as bleach and/or oxidation catalysts.

BACKGROUND

Manganese complexes containing the ligands $Me_3$-TACN (1,4,7-trimethyl-1,4,7-triazacyclononane) and $Me_4$-DTNE (1,2-bis-(4,7-dimethyl-1,4,7-triazacyclonon-1-yl)-ethane) are of interest for different bleaching of cellulosic and other substrates.

Different methods have been disclosed to synthesise 1,4-ditosyl-1,4,7-triazacyclononane ($Ts_2$-TACN) from 1,4,7-tritosyl-1,4,7-triazacyclononane ($Ts_3$-TACN) as described below.

$Ts_3$-TACN has been treated with a mixture of bromic acid and acetic acid for 20 h at 100° C. and subsequently refluxed for 30 h to yield fully detosylated 1,4,7-triazacyclononane ($H_3$-TACN) as HBr salt, i.e. $H_3$-TACN.HBr; subsequent reaction with 2 equivalents of tosyl chloride afforded $Ts_2$-TACN in 60% yield as disclosed in *Inorg. Chem.*, 1985, 24, 1230.

$Ts_3$-TACN has been treated with a mixture of bromic acid, acetic acid and phenol for 36 h at 90° C., to furnish monotosylated Ts-TACN. Further reaction with 1 equivalent of tosyl chloride to afford $Ts_2$-TACN in a higher yield than using method 1-76% as disclosed in *Inorg. Chem.*, 1990, 29, 4143.

$Ts_3$-TACN has been heated with a mixture of hydrobromic acid and acetic acid under reflux for 3 h to yield a mixture of Ts-TACN.HBr (68%) and $Ts_2$-TACN.HBr(30%) as disclosed in *Synthetic Communications*, 2001, 31(20), 3141.

Isolation of protonated $Ts_2$-TACN salt with bromide as counter ion has been described in *Synthetic Communications* 31(20), 3141-3144, 2001; and US 2005/112066 A1.

The reaction of $Ts_2$-TACN with 2 equivalents of ditosylethyleneglycol in DMF to yield 1,2-bis(4,7-ditosyl-1,4,7-triazacyclonon-1-yl)-ethane ($Ts_4$-DTNE) is also disclosed in *Inorg. Chem.* 1985, 24, 1230; *Inorg. Chem.* 1996, 35, 1974-1979; *Inorg. Chem.* 1998, 37(5), 3705-3713; *Inorg. Chem.* 2005, 44 (2), 401-409; and *J. Chem. Soc., Dalton Trans.* 1994, 457-464.

$Ts_4$-DTNE has also been obtained using O,O',N,N'-tetratosyl-N,N'-bis(2-hydroxyethylethylenediamine and ethylenediamine (*Synthesis* 2001, 2381-2383; *Inorg. Chem.* 2007, 46(1), 238-250; *Green Chem.* 2007, 9, 996-1007).

Synthesis of 1,2-bis(1,4,7-triazacyclonon-1-yl)-ethane (DTNE) from methine-1,4,7-triazacyclononane and dibromoethane or diiodoethane has been disclosed in *J. Chem. Soc., Chem. Commun.*, 1987, 886; *J. Am. Chem. Soc.*, 1998, 120, 13104-13120; *Inorg. Chem.* 1993, 32, 4300-4305; *Inorg. Chem.* 1997, 36, 3125-3132; *Chem. Lett.* 2000, 416-417; *J. Chem. Soc., Dalton Trans.*, 2000, 3034-3040.

Synthesis of $Me_4$-DTNE from DTNE using formaldehyde and formic acid can be found in *J. Am. Chem. Soc.*, 1998, 120, 13104-13120; *Inorg. Chem.* 1993, 32(20), 4300-4305; *Chem. Lett.*, 2000, 416-7.

Using the known methods, the binucleating triazacyclononane ligand can be obtained in a reasonable yield. However, as the purity level is insufficient to obtain the dinuclear manganese complex ($[Mn^{IV}Mn^{III}$ ($\mu$-O)$_2$($\mu$-OAc)($Me_4$-DTNE)$]^{2+}$) in high yield, an additional purification step, such as vacuum destillation is needed. Although this gives then a high purity material, the yield loss is quite substantial. Therefore there is still a need to be able to synthesise manganese complexes using $Me_4$-DTNE that has been obtained in a more simple synthetic procedure, with preferably without needing to distil $Me_4$-DTNE prior complexation.

SUMMARY

We have found that partial detosylation of $Ts_3$-TACN in a one-pot process leads to the formation of $Ts_2$-TACN as its protonated salt. This is an improvement over the two-step process of complete detosylation of $Ts_3$-TACN followed by ditosylation of the TACN adduct. Furthermore, less tosyl chloride can be used to make $Ts_2$-TACN and less tosylate waste compared to the above route has been obtained.

In a first aspect the present invention provides a method of producing a compound of formula (A):

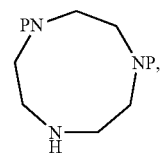

(A)

the method comprising the following step:
(a) reacting a compound of formula (B):

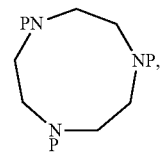

(B)

in an acidic medium comprising sulfuric acid, the molar ratio of B to sulfuric acid in the range from 1:0.1 to 1:10, preferably 1:0.5 to 1:10, more preferably 1:0.5 to 1:5, even more preferably from 1:1 to 1:4, wherein P is an arylsulfonate protecting group and the compound of formula (A) is isolated as a protonated salt in amorphous or crystalline form.

In a second aspect the present invention provides a method of producing a compound of formula (A):

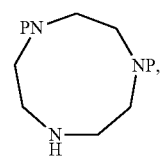

(A)

the method comprising the following step:
(a) reacting a compound of formula (B):

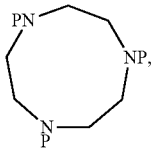
(B)

in an acidic medium, wherein P is an arylsulfonate protecting group, wherein the acidic medium is worked-up when the conversion of B to A is at least 50 mol % yielding compound (A).

As disclosed in the background of invention the Ts$_2$-TACN may be used to form Ts$_4$-DTNE which can be detosylated and secondary amines of the product methylated in a similar fashion described in U.S. Pat. No. 5,284,944 for Ts$_3$-TACN. In a similar manner the same applies to the arylsulfonates as a class of protecting groups. Such reactions relate to further aspects of the invention.

Reaction of 1,4-di(arylsulfonate)-1,4,7-triazacyclonane ((ArSO$_2$)$_2$-TACN) with dihaloethane in a solvent, optionally, in the presence of water, and a base yields 1,2-bis-(4,7-diarylsulfonate-1,4,7-triazacyclonon-1-yl)-ethane in high yield. Removing the arylsulfonate protecting groups and then reacting further with formaldehyde and formic acid in one-pot reaction yields Me$_4$-DTNE. Surprisingly, when acetonitrile/water is employed as a solvent in the step to form Ts$_4$-DTNE, the purity level of Me$_4$-DTNE is high enough to allow complexation to form the manganese complex, ([Mn$^{IV}$Mn$^{III}$(μ-O)$_2$ (μ-OAc)(Me$_4$-DTNE)]$^{2+}$), without the need to distil the Me$_4$-DTNE ligand prior the complexation step.

In a third aspect the present invention provides a method of producing a compound of formula (C), the method comprising the following step:

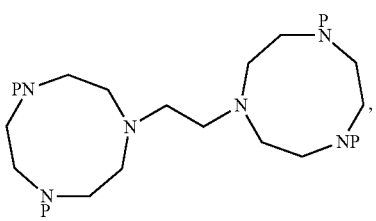
(C)

(a) reacting a compound of formula (A):

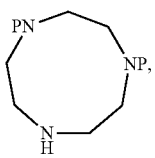
(A)

with a bridging element of the form ZCH$_2$CH$_2$Z, wherein P is an arylsulfonate protecting group and Z is a halogen selected from: Cl; Br; and, I.

In chemistry one-pot synthesis/reaction is a strategy to improve the efficiency of a chemical reaction whereby a reactant is subjected to successive chemical reactions in just one reactor. This is much desired by chemists because avoiding a lengthy separation process and purification of the intermediate chemical compound would save time and resources while increasing chemical yield.

In a fourth aspect the present invention provides a one-pot method for the preparation of Me$_4$-DTNE, the method comprising deprotecting a compound of formula (C):

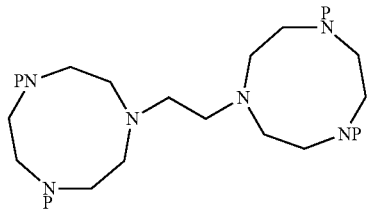
(C)

with an acidic medium and to form DTNE and subsequently adding formaldehyde and formic acid to the reaction medium, wherein P is an arylsulfonate.

DETAILED DESCRIPTION

The starting material 1,4,7-tri(arylsulfonate)-1,4,7-triazacyclonane ((ArSO$_2$)$_3$-TACN) is reacted in acid to yield ((ArSO$_2$)$_2$-TACN).

A preferred synthetic scheme for obtaining an (ArSO$_2$)$_2$-TACN (Ts$_2$-TACN) is outlined below.

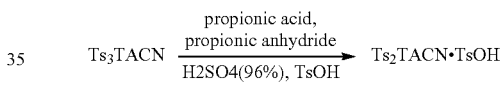

The preferred temperature range for monodearylsulfonation of the triarylsulfonate is from 100 to 160° C., with most preferred from 130 and 150° C.

The preferred time for the method is from 1 h to 24 h, the most preferred time from 2 to 6 h.

Preferably the method is conducted as a one-pot reaction.

The preferred acid for monodearylsulfonation of the tri arylsulfonate is sulfuric acid. Other acids, such as methanesulfonic acid and sulfonic acid resins may function to provide the monodetosylation. Preferably, the acidic medium does not contain any hydrogen halides and in this regard, the acidic medium preferably has less than 1 mol % hydrogen halides with respect to B. We have surprisingly found that use of such acidic media provides advantages in relation to the use of hydrogen halides. In particular, whereas the use of a mixture of acetic acid and hydrobromic acid has been reported to provide a mixture of mono- and ditosylated (predominantly monotosylated) TACN from Ts$_3$-TACN (*Synthetic Communications*, 2001, 31(20), 3141), the present invention advantageously, and surprisingly, permits the provision of a significantly higher proportion of the desired ditosylated (monodetosylated) product.

Additionally auxiliary anhydrides are preferably present, such as acetic acid anhydride or propionic acid anhydride when excess water is present in the reaction mixture. The amount of acid anhydride required to facilitate the reaction depends upon the amount of water initially present in the reaction.

The use of an auxiliary anhydride in a method of producing a compound of formula (A) as hereinbefore defined represents a fifth aspect of the present invention. Viewed from the suspect, the invention provides a method of producing a compound of formula (A), as hereinbefore defined, comprising reacting a compound of formula (B) in an acidic medium comprising an acid anhydride. The acidic medium may be as described herein and the compound of formula (A) is typically isolated as a protonated salt, such as an aryl sulfonic acid salt (e.g. the toluene sulfonic acid or benzene sulfonic acid salt), for example in amorphous or crystalline form.

The acid anhydride serve to maintain the molar ratio of $(ArSO_2)_3$-TACN:water at a level that aids the ideal molar ratio for the reaction, namely 1:1.

The optimum amount of acid anhydride to be added to the reaction mixture is dependent on the amount of $(ArSO_2)_3$-TACN and the amount of water in the system (originating from the water present in $(ArSO_2)_3$-TACN and sulfuric acid added). If the molar amount of water present in $(ArSO_2)_3$-TACN and sulfuric acid is much larger than the molar amount of $(ArSO_2)_3$-TACN, the reaction may become less efficient, i.e. more mono(arylsulfonate)TACN or $H_3$-TACN will be formed. It should be noted that one mol of acid anhydride will react with one mol of water to form two moles of acid.

Therefore, the following relation exists (all on molar basis):

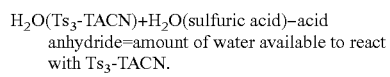

Therefore:

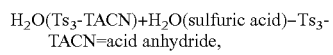

which is equal to:

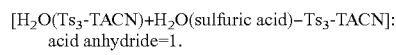

Allowing variables in process conditions, this ratio should be varying between 0.1 and 10, more preferably between 0.3 and 5 and most preferably between 0.8 and 2.

It is preferred that a tosyl group is used as protecting group for the secondary amines of the TACN moiety. The tosyl group (abbreviated Ts or Tos) is $CH_3C_6H_4SO_2$. This group is usually derived from the compound 4-toluene sulfonyl chloride, $CH_3C_6H_4SO_2Cl$, which forms esters and amides of toluene sulfonic acid. The para orientation illustrated (p-toluenesulfonyl) is most common, and by convention tosyl refers to the p-toluenesulfonyl group. Tosylate refers to the anion of p-toluenesulfonic acid ($CH_3C_6H_4SO_3$). Whilst the tosyl group is the preferred protecting group, other arylsulfonyl groups ($ArSO_2$) will function to provide the advantages of the present invention. Preferably the arylsulfonyl employed is a benzenesulfonate. The skilled person will understand that, where compounds of formula (A) are prepared from compounds of formula (B) and isolated as a protonated salt, the protonated salt will typically be of the same arylsulfonic acid (e.g. p-toluene sulfonic acid) of which protecting group Pin compounds of formulae (A) and (B) is the aryl sulfonate.

Compared to the known procedures to make $Ts_2$-TACN, as outlined in the background of the invention, there will be one-step less needed to obtain this material in a high yield and purity. Furthermore, less tosylchloride (arylsulfonate) starting materials are needed to form $(ArSO_2)_2$-TACN (3 instead of 5 molar equivalents) and as a consequence also less tosylate (arylsulfonate) waste will be generated.

In a sixth aspect of the invention the $(ArSO_2)_2$-TACN can be obtained and isolated as a protonated (HX) salt in which HX is selected from: toluenesulfonic acid; benzenesulfonic acid; sulfuric acid; acetic acid; formic acid; and, propionic acid, most preferably from toluenesulfonic acid, benzenesulfonic acid and sulfuric acid. One skilled in the art will appreciate that some acids will support more than one protonated $(ArSO_2)_2$-TACN, for example sulfuric acid. Alternatively, sulfuric acid may support one protonated $(ArSO_2)_2$-TACN, as the $HSO_4^-$ counterion. According to particular embodiments of this and other aspects of the invention, the protonated salt of the $(ArSO_2)_2$-TACN is $Ts_2$-TACN.TsOH (wherein TsOH is toluene sulfonic acid), or the benzene sulfonic acid salt of 1,4-di(benzenesulfonate)-1,4,7-triazacyclononane.

From the disclosure it will be evident that conditions and some reagents may be varied to provide the desired $(ArSO_2)_2$-TACN. With this in mind, one skilled in the art can monitor the progress of the reaction, for example by thin layer chromatography, and determine the extent to which $(ArSO_2)_2$-TACN. When the conversion of B ($(ArSO_2)_3$-TACN) to A ($(ArSO_2)_2$-TACN) is at least 50 mol % yielding compound (A) the reaction is worked-up, Preferably, the reaction is worked up when the conversion of B to A is at least is at least 50 mol % yielding compound (A).

The term worked-up is known in the art. In chemistry work-up refers to the series of manipulations required to isolate and purify the product(s) of a chemical reaction. Typically, these manipulations include:
- quenching a reaction to deactivate any unreacted reagents changing the pH to prevent further reaction
- cooling the reaction mixture or adding an antisolvent to induce precipitation, and collecting or removing the solids by filtration, decantation, or centrifuging
- removal of solvents by evaporation
- separating the reaction mixture into organic and aqueous layers by liquid-liquid extraction
- purification by chromatography, distillation or recrystalisation.

A method for obtaining $Me_4$-DTNE is also provided.

A preferred synthetic scheme for obtaining $Me_4$-DTNE is outlined below.

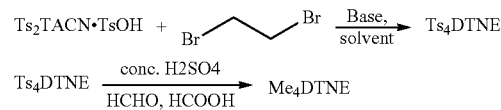

The $(ArSO_2)_2$-TACN (e.g. $Ts_2$-TACN) in particular embodiments of this invention is prepared according to the first or second aspects of the invention and/or be a protonated salt in accordance with the sixth aspect of the invention, for example $Ts_2$-TACN.TsOH. In the discussion of the invention herein, focus is primarily upon embodiments of the present invention for obtaining $Me_4$-DTNE using $Ts_2$-TACN.TsOH. However, the invention is not limited to these embodiments, since the skilled person is aware of other ways of making $(ArSO_2)_2$-TACN, and protonated salts thereof, including $Ts_2$-TACN and protonated salts thereof, for example in accordance with the documents referred to in the Background section.

$(ArSO_2)_2$-TACN reacts with 1,2-dihaloethane in a solvent and a base, wherein the water level in the solvent is between 0 and 90%. The 1,2-dihaloethane is preferably selected from 1,2-dibromoethane, 1,2-diodoethane and 1,2-dichloroethane, with 1,2-dibromoethane being most preferred. Different solvents can be employed, such as acetonitrile, dimethylformamide (DMF), xylene, toluene, dioxane, 1-butanol, 2-butanol, t-butanol, 1-propanol, and 2-propanol. The solvent may contain additional water. The water content of the solvent may be between 0 and 90%.

The base used for the coupling of (ArSO$_2$)$_2$-TACN with dihaloethane should not be too strong; the base used for the coupling reaction is preferably sodium carbonate.

It is preferred that a tosyl group is used as protecting group for the secondary amines of the TACN moiety.

Preferred solvents are acetonitrile, 1-butanol, 2-butanol, t-butanol, and dimethylformamide (DMF). These solvent are preferably used with additional water, preferably between 10 and 90%. Most preferably, acetonitrile/H$_2$O is used, as 1,2-bis(4,7-arylsulfonate-1,4,7-triazacyclonon-1-yl)-ethane obtained is of higher purity than using other solvents. This allows the formation of the Me$_4$-DTNE ligand of higher purity and therefore the ligand does not need to be distilled prior using for the complexation step with manganese.

The protecting groups of 1,2-bis(4,7-arylsulfonate-1,4,7-triazacyclonon-1-yl)-ethane are removed by treatment with an acid to yield DTNE. The preferred acid used for deprotection is concentrated sulfuric acid. After deprotection the solution containing the deprotected ligand is neutralised to pH 5 to 9, preferably pH 6 to 8.

The DTNE is preferably methylated by reaction with formaldehyde and subsequent reduction. In this regard, reaction with formaldehyde and formic acid (Eschweiler-Clarke methylation) are the preferred reagents to effect methylation. This reductive amination step will not produce quaternary ammonium salts, but instead will stop at the tertiary amine stage. For the aforementioned reason the Eschweiler-Clarke methylation is preferred over other methylation procedures.

Whilst the Eschweiler-Clarke methylation step is preferred other methylation reactions may be used. Methylation of secondary amines is well known in the art. Some examples of references are Ber. 1905, 38, 880; J. Am. Chem. Soc., 1933, 55, 4571; J. Org. Chem. 1972, 37(10), 1673-1674; J. Chem. Soc., Perkin Trans 1, 1994, (1), 1-2; Synth. Commun., 2002, 32(3), 457-465; Synth. Commun., 1989, 19(20), 3561-3571; Synth. Commun., 2006, 36(23), 3609-3615; EP0553954A2; U.S. Pat. No. 5,105,013; J. of the Indian Chemical Society 1967, 44(5), 430-435; J. of the Indian Chemical Society 1970, 8(8), 725-727.

Reductive methylation in general applying formaldehyde and a reducing agent like cyanoborohydride, formic acid, molecular hydrogen and a catalyst (Nickel, Palladium on coal, etc.) can be employed. Also direct methylation with methyl-X (X=Cl, Br, I).

Catalytic conversions for preparing tertiary amines from secondary and primary amines using hydrogen gas and formaldehyde can be for example found in U.S. Pat. No. 4,757,144.

After the methylation is reaction is complete, increasing the pH to preferably higher than 12, more preferably higher than 13, the Me$_4$-DTNE ligand can be extracted using a C5-C8 hydrocarbon as solvent. The C5-C8 is preferably selected from pentane, hexane, heptane, octane, cyclopentane, cyclohexane, cycloheptane, cyclooctane, toluene, xylene and combinations thereof. Most preferred solvents are hexane or heptane. When not using acetonitrile to synthesise 1,2-bis-(4,7-arylsulfonate-1,4,7-triazacyclonon-1-yl)-ethane, the ligand obtained is best vacuum distilled before further complexing with manganese salts. Alternatively, the ligand may be purified by precipitating as HCl salt, after which the free Me$_4$-DTNE ligand was obtained by addition of concentrated NaOH solution, as exemplified in J. Am. Chem. Soc. 1998, 120, 13104-13120.

The invention may be further understood with respect to the following non-limiting clauses:

1. A method of producing a compound of formula (A):

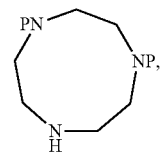

(A)

the method comprising the following step:
(a) reacting a compound of formula (B):

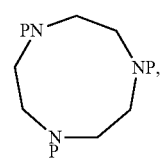

(B)

in an acidic medium comprising sulfuric acid, the molar ratio of B to sulfuric acid in the range from 1:0.5 to 1:10, wherein P is an arylsulfonate protecting group and the compound of formula (A) is isolated as a protonated salt in amorphous or crystalline form.

2. A method of producing a compound of formula (A):

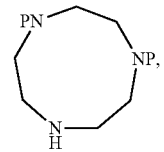

(A)

the method comprising the following step:
(a) reacting a compound of formula (B):

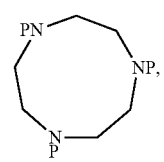

(B)

in an acidic medium, wherein P is an arylsulfonate protecting group, wherein the acidic medium is worked-up when the conversion of B to A is at least 50 mol % yielding compound (A).

3. The method of clause 1 or clause 2, wherein an acid anhydride is present in the acidic medium.

4. A method of producing a compound of formula (A):

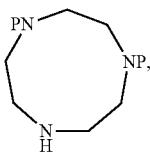
(A)

the method comprising reacting a compound of formula (B):

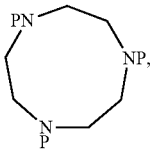
(B)

in an acidic medium comprising an acid anydride, wherein P is an arylsulfonate protecting group.

5. The method of any one of clauses 2 to 4, wherein the compound of formula (A) is isolated as a protonated salt of the same arylsulfonic acid of which P is the arylsulfonate.

6. The method of clause 5, wherein the protonated salt of the compound of formula (A) is isolated in amorphous or crystalline form.

7. The method of any one of clauses 2 to 6, wherein the acidic medium comprises sulfuric acid.

8. The method of any one of clauses 1 or 3 to 7, wherein the protonated salt is a salt of an aryl sulfonic acid.

9. The method of clause 8, wherein the protonated salt is:
   (i) (1,4-ditosyl-1,4,7-triazacyclonone) tosylate (which is the toluene sulfonic acid salt of 1,4-ditosyl-1,4,7-triazacyclononane); or
   (ii) (1,4-dibenzenesulfonyl-1,4,7-triazacyclonone)benzenesulfonate (which is the benzene sulfonic acid salt of 1,4-dibenzene sulfonyl-1,4,7-triazacyclononane).

10. The method of any one preceding clause, wherein the method is conducted at a reaction temperature from 100 to 160° C.

11. The method of any one preceding clause, further comprising reacting a compound of formula (A) with a bridging element of the form ZCH$_2$CH$_2$Z, wherein Z is a halogen selected from: Cl; Br; and, I, whereby to produce a compound of formula (C):

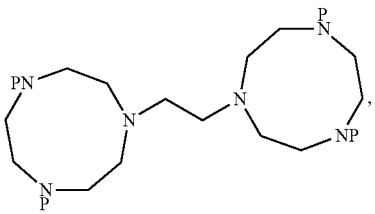
(C)

wherein groups P in the compound of formula (C) are the same as groups P in the compound of formula (A).

12. The method of clause 11, wherein the compound of formula (A) is reacted with the bridging element in acetonitrile, for example aqueous acetonitrile, such as aqueous acetonitrile comprising from 10 to 90 wt/wt % water, from 10 to 50 wt/wt % water or from 10 to 35 wt/wt % water.

13. The method of clause 11 or clause 12 further comprising, optionally in a one-pot method, deprotecting the compound of formula (C) with an acidic medium to form 1,2-bis(1,4,7-triazacyclonon-1-yl)-ethane and subsequently adding formaldehyde and formic acid to the reaction medium whereby to produce 1,2-bis-(4,7-dimethyl-1,4,7-triazacyclonon-1-yl)-ethane.

14. A protonated salt of formula (A), having a counter ion HX, the protonated salt in amorphous or crystalline form:

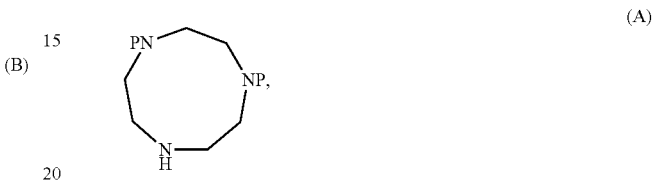
(A)

wherein P is a tosylate or benzene sulfonate and HX is selected from: toluenesulfonic acid; benzenesulfonic acid; sulfuric acid; acetic acid; formic acid; and, propionic acid.

15. The protonated salt of clause 14, which is (1,4-ditosyl-1, 4,7-triazacyclonone) tosylate, (1,4-dibenzenesulfonyl-1,4,7-triazacyclonone)benzenesulfonate or (1,4-ditosyl-1,4,7-triazacyclonone)benzenesulfonate.

16. The protonated salt of clause 14, which is (1,4-ditosyl-1, 4,7-triazacyclonone) tosylate.

17. The protonated salt of clause 14, which is (1,4-dibenzenesulfonyl-1,4,7-triazacyclonone)benzenesulfonate.

18. A method of producing a compound of formula (C):

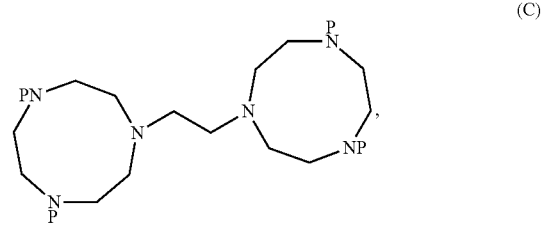
(C)

the method comprising the following step:
(a) reacting a compound of formula (A):

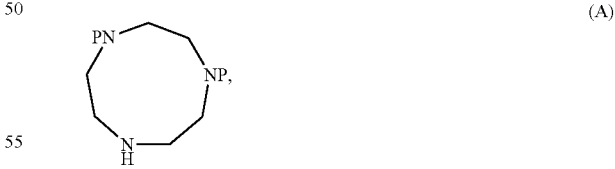
(A)

with a bridging element of the form ZCH$_2$CH$_2$Z, wherein P is an arylsulfonate protecting group and Z is a halogen selected from: Cl; Br; and, I.

19. The method of clause 18, wherein the compound of formula (A) is reacted with the bridging element in a solvent selected from: acetonitrile; 1-butanol; 2-butanol; and, t-butanol.

20. The method of clause 19, wherein the compound of formula (A) is reacted with the bridging element in acetonitrile as solvent, for example with aqueous acetonitrile as solvent.

21. The method of clause 20, wherein the solvent comprises from 10 to 90 wt/wt % water, from 10 to 50 wt/wt % water, or from 10 to 35 wt/wt % water.

22. The method of any one of clauses 18 to 21, wherein the method further comprises, optionally in a one-pot method, deprotecting the compound of formula (C) with an acidic medium to form 1,2-bis(1,4,7-triazacyclonon-1-yl)-ethane and subsequently adding formaldehyde and formic acid to the reaction medium whereby to produce 1,2-bis-(4,7-dimethyl-1,4,7-triazacyclonon-1-yl)-ethane.

23. A one-pot method for the preparation of 1,2-bis-(4,7-dimethyl-1,4,7-triazacyclonon-1-yl)-ethane (Me$_4$-DTNE) the method comprising deprotecting a compound of formula (C).

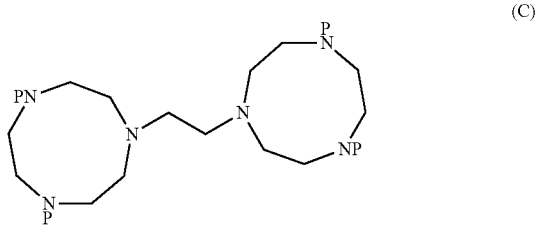

(C)

with an acidic medium and to form 1,2-bis(1,4,7-triazacyclonon-1-yl)-ethane and subsequently adding formaldehyde and formic acid to the reaction medium, wherein P is an arylsulfonate.

24. The one-pot method of clause 23, wherein P is tosylate.

The following examples illustrate the invention more fully in which the amounts and ratios as given herein apply to the start of the method and will change during the reaction; and Ts$_2$-TACN TsOH used in Examples 2, 3a & 3b, 5a-5c and 7-10 was prepared according to Example 1.

EXPERIMENTAL

1 Preparation of Ts$_2$-TACN.TsOH

Ts$_3$-TACN was synthesised as disclosed in WO9400439. Ts$_3$-TACN (128.3 g, 96.6% containing 3.4% water, 209.5 mmol of Ts$_3$-TACN, 242 mmol H$_2$O) and propionic acid (113 mL) were placed in a 500 mL three-necked-flask with thermometer and condenser. While stirring magnetically and warming (bath 160-170° C.) most of the Ts$_3$-TACN dissolved. Propionic anhydride (12 g, 92 mmol) and sulfuric acid (29.5 mL, 96%, 530 mmol, containing 120 mmol H$_2$O) were then added. (Caution: at the beginning period of adding H$_2$SO$_4$, exothermic reaction occurred violently). Stirring was continued (reaction mixture=142-143° C.) until the TLC showed the conversion to be complete (about 3 hrs). After partial cooling, the warm (70~80° C.) contents of the flask were poured into 1.5 L ice-water while stirring vigorously. The product was left at room temperature overnight, then filtered over a large frit (φ10 cm) and washed with water (6×300 mL) until pH=7, the obtained white solid was dried under vacuum at 60° C. with P$_2$O$_5$ until the weight is constant (at least 2 days). Yield of Ts$_2$-TACN.TsOH: 93 g (74%) with purity: 91.5%. The filtrate was neutralized with aqueous NaOH to pH14, white solid which proved to be Ts$_2$-TACN appeared, filtered and washed with water, dried under vacuum to a constant weight. Another 4% product could be obtained with 90% purity. The total yield is about 78%.

$^1$H NMR (400 MHz, CDCl$_3$): δ 2.36 (s, [ArCH$_3$ (TsOH), 3H]), 2.44 (s, (ArCH$_3$ (N-Ts), 6H), 3.41 (br.s, [N—CH$_2$, 4H]), 3.54 (br.s, [N—CH$_2$, 4H]), 3.75 (br. S, [N—CH2, 4H]), 7.20 (d, J=7.4 Hz, [ArH, 2H]), 7.32 (d, J=7.4 Hz, [ArH, 4H]), 7.66 (d, J=7.4 Hz, [ArH, 4H]), 7.90 (d, J=7.4 Hz, [ArH, 2H]).

ESI-MS (ES+): m/z 438 (Ts2-TACN+H)$^+$

2 Preparation of Ts$_4$-DTNE Using Acetonitrile as Aprotic Solvent

Ts$_4$-DTNE=1,2-bis(4,7-ditosyl-1,4,7-triazacyclonon-1-yl)-ethane

The mixture of the protonated tosylate salt of 1,4-ditosyl-1,4,7-triazacyclonone (Ts$_2$-TACN.TsOH –3.0 g, 5 mmol) and Na$_2$CO$_3$ (2.12 g, 20 mmol) in 20 mL acetonitrile was stirred under reflux for 5 min. Then 1,2-dibromoethane (0.43 mL, 5 mmol) was added and the resulting mixture was refluxed overnight (TLC showed the completion of the reaction, CH$_2$Cl$_2$/methanol (97:3)). Then the solvent was evaporated and to the residue 50 mL water was added and the resulting mixture was filtered. The solid was washed with water (4×50 mL), dried under vacuum to afford the product 1.84 g (84%) with 84% purity.

$^1$H NMR (400 MHz, CDCl$_3$):
1.42 (s, [ArCH3, 12H]), 2.73 (s, [bridging N—CH2, 4H]), 2.93 (s, 8H), 3.19 (s, 8H), 3.46 (s, 8H), 7.30 (d, J=7.4 Hz, 8H), 7.65 (d, J=7.4 Hz, 8H).

ESI-MS (ES+): m/z 901(M+H)$^+$

3a Preparation of Ts$_4$-DTNE in Acetonitrile/Water

The mixture of Ts$_2$-TACN TsOH (3.0 g, 5 mmol) in 25 mL acetonitrile and Na$_2$CO$_3$ (2.12 g, 20 mmol) in 10 mL water was stirred at 100° C. for 5 min. Then 1,2-dibromoethane (0.43 mL, 5 mmol) was added and the resulting mixture was refluxed overnight (TLC showed the completion of the reaction, CH$_2$Cl$_2$/methanol (97:3)). After being cooled to room temperature, the mixture was poured into 50 mL water and was filtered. The solid was washed with water (4×50 mL), dried under vacuum to afford the product 1.6 g (72%) with 93.3% purity.

3b Preparation of Ts$_4$-DTNE in acetonitrile/water (larger scale)

The mixture of Ts$_2$-TACN TsOH (60 g, 100 mmol) in 500 mL acetonitrile and Na$_2$CO$_3$ (42.5 g, 400 mmol) in 200 mL water was stirred at 100° C. for 5 min. Then 1,2-dibromoethane (8.75 mL, 100 mmol) was added and the resulting mixture was refluxed overnight (TLC showed the completion of the reaction, CH$_2$Cl$_2$/methanol (97:3)). After being cooled to room temperature, the mixture was poured into ca. 1000 mL water and was filtered. The solid was washed with water (4×1000 mL), dried under vacuum to afford the product 33 g (74.6%) with 93.3% purity.

4a Preparation of Me$_4$-DTNE Using Ts$_4$-DTNE Prepared in Acetonitrile/H$_2$O

Ts$_4$-DTNE (93.3% purity) (25 g, 26 mmol) and 96% sulfuric acid (59.2 mL, composed of 56.8 mL concentrated H$_2$SO$_4$ (98%) plus 2.4 mL water) were stirred at 110° C. (oil bath) in a 1 L 3-necked flask overnight. The reactants were cooled to 50° C., then water (71 mL) and NaOH solution (108 g NaOH in 200 mL water) was added dropwise under ice-bath with stirring until pH=6~7, then formaldehyde (25.3 g(37%)) and formic acid (99%) (28.7 g) were added successively with stirring, the mixture was stirred at 90~100° C. (110° C. oil bath) overnight, then cooled to room temperature, the contents were made strongly alkaline by adding NaOH (32 g in 60 mL water) until pH 14 while maintaining the temperature at 30° C., the brown slurry was stirred efficiently with hexane (200 mL) then filtered over celite. After separating the phase, the filter cake was washed with hexane (4×200 mL) which was subsequently used to extract the aqueous, then the aqueous was extracted with hexane (4×500 mL), the combined hexane layer was evaporated to get the crude product 7.4 g (84%) as yellow oil with purity 85%. Similar results were obtained when heptane was used as the extraction solvent.

$^1$H NMR (400 MHz, CDCl$_3$): 2.3 (s, 12H, —CH3), 2.6 (m, 28H, —N—CH2). ESI-MS (ES+): m/z 341 (M+H)$^+$.

4b Preparation of Me$_4$-DTNE Using Ts$_4$-DTNE Prepared in Acetonitrile/H$_2$O Ts$_4$-DTNE obtained in step 2 (93.3% purity) (21.5 g, 22.4 mmol) and 96% sulfuric acid (54.7 mL, composed of 52.5 mL concentrated H$_2$SO$_4$ (98%) plus 2.2 mL water) were stirred at 110° C. (oil bath) in a 1 L 3-necked flask overnight. The reactants were cooled to 50° C., then water (59 mL) and NaOH solution (90 g NaOH in 150 mL water) was added dropwise under ice-bath with stirring until pH=6-7, then formaldehyde (27 mL(37%)) and formic acid (99%) (20 mL) were added successively with stirring, the mixture was stirred at 90-100° C. (110° C. oil bath) overnight, then cooled to room temperature, 59 mL water was added and the contents were made strongly alkaline by adding NaOH (27 g in 50 mL water) until pH 14 while maintaining the temperature at 30° C., the brown slurry was stirred efficiently with hexane (200 mL) then filtered over celite. After separating the phase, the filter cake was washed with hexane (4×200 mL) which was subsequently used to extract the aqueous layer (4×400 mL), the combined hexane layer was evaporated to get the crude product 6.7 g (88.4%) as yellow oil with purity 84% and 5.2% Me$_3$-TACN and 10.8% unknown impurities included.

5a Preparation of Ts$_4$-DTNE in Butanol/Water

The mixture of Ts$_2$-TACN TsOH (3.0 g, 5 mmol) and Na$_2$CO$_3$ (2.12 g, 20 mmol) in 10 mL water and 1.7 mL butanol was stirred at 115° C. for 5 min. Then 1,2-dibromoethane (0.43 mL, 5 mmol) was added and the resulting mixture was refluxed for 3 hrs (TLC showed the completion of the reaction, CH$_2$Cl$_2$/methanol (97:3)). After being cooled to room temperature, the mixture was poured into 50 mL water and was filtered. The solid was washed with water (4×50 mL), dried under vacuum to afford the product 2.06 g (94%) with 75% purity.

5b Preparation of Ts$_4$-DTNE in Butanol/Water

The mixture of Ts$_2$-TACN TsOH (157.5 g, 262.5 mmol) and Na$_2$CO$_3$ (106 g, 1 mol) in 360 mL water and 61 mL butanol was stirred at 115° C. for 5 min. Then 1,2-dibromoethane (20.8 mL, 242 mmol) was added and the resulting mixture was refluxed for 3 hrs (TLC showed the completion of the reaction, CH$_2$Cl$_2$/methanol (97:3)). After being cooled to room temperature, the mixture was poured into 1500 mL water and was filtered. The solid was washed with water (4×1500 mL) to pH 7, dried under vacuum to afford the product 115.9 g (98%) with 75.6% purity.

5c Preparation of Ts$_4$-DTNE in Butanol/Water

A similar procedure to Experiment 5a was followed to make another batch of Ts$_4$-DTNE by reacting Ts$_2$-TACN.TsOH (91.5 g) in butanol/water to afford 68.7 g (100%) Ts$_4$-DTNE having a purity of 77%.

6a Preparation of Me$_4$-DTNE Using Ts$_4$-DTNE Prepared in Butanol/Water

Ts$_4$-DTNE (52 g (77% purity), 44.5 mmol) and 96% sulfuric acid (130.6 mL, composed of 125.6 mL concentrated H$_2$SO$_4$ (98%) plus 5 ml water) were stirred at 110° C. (bath) in a 1 L 3-necked flask until TLC showed the detosylation to be completed (about 22 hrs). The reactants were cooled to 50° C., then water (121 mL) and NaOH solution (4.63 mol, 185 g NaOH in 230 mL water) was added dropwise under ice-bath with stirring until pH=6~7, then formaldehyde (0.693 mol, 56.6 g(37%)) and formic acid (1.626 mol, 64 g) were added successively with stirring, the mixture was stirred at 90° C. (110° C. oil bath) overnight, then cooled to room temperature, the contents were made strongly alkaline by adding NaOH (56 g in 68 mL water) while maintaining the temperature at 30° C., the brown slurry was stirred efficiently with hexane (300 mL) then filtered over celite. After separating the phase, the filter cake was washed with hexane (6×200 mL) which was subsequently used to extract the aqueous solution, then the aqueous solution was extracted with hexane (4×500 mL), the combined hexane was evaporated to get the crude product 13.53 g as an yellow oil which was redistilled under reduced pressure to afford the product 8.3 g (55%) at 136~138° C./1 mbar as a pale yellow liquid with purity 93%.

6b Preparation of Non-Distilled Me$_4$-DTNE Using Ts$_4$-DTNE Prepared in Butanol/Water Ts$_4$-DTNE obtained in step 5b (60 g (75.6% purity), 51.2 mmol) and 96% sulfuric acid (143.5 mL, composed of 138 mL concentrated H$_2$SO$_4$ (98%) plus 5.5 ml water) were stirred at 110° C. (bath) in a 1 L 3-necked flask until TLC showed the detosylation to be completed (about 22 hrs). The reactants were cooled to 50° C., then water (120 mL) and NaOH solution (198 g NaOH in 300 mL water) was added dropwise under ice-bath with stirring until pH=6~7, then formaldehyde (74 mL(37%)) and formic acid (56 mL) were added successively with stirring, the mixture was stirred at 90° C. (110° C. oil bath) overnight, then cooled to room temperature, the contents were made strongly alkaline by adding NaOH (61.5 g in 78 mL water) while maintaining the temperature at 30° C., the brown slurry was stirred efficiently with hexane (300 mL) then filtered over celite. After separating the phase, the filter cake was washed with hexane (6×200 mL) which was subsequently used to extract the aqueous solution (4×500 mL), the combined hexane was evaporated and the residue was dried under vacuum to afford the crude product 8.2 g (48%) as a yellow oil with purity 70.5%. The product contains 22.5% Me$_3$-TACN.

6c Preparation of Distilled Me$_4$-DTNE Using Ts$_4$-DTNE Prepared in Butanol/Water Ts$_4$-DTNE obtained in step 5c (54 g (77% purity), 46.2 mmol) and 96% sulfuric acid (132 mL, composed of 127 mL concentrated H$_2$SO$_4$ (98%) plus 5 ml water) were stirred at 110° C. (bath) in a 1 L 3-necked flask until TLC showed the detosylation to be completed (about 22 hrs). The reactants were cooled to 50° C., then water (121 mL) and NaOH solution (4.63 mol, 185 g NaOH in 230 mL water) was added dropwise under ice-bath with stirring until pH=6~7, then formaldehyde (69 mL/37/%) and formic acid (52 mL) were added successively with stirring, the mixture was stirred at 90° C. (110° C. oil bath) overnight, then cooled to room temperature, the contents were made strongly alkaline by adding NaOH (55.5 g in 70 mL water) while maintaining the temperature at 30° C., the brown slurry was stirred efficiently with hexane (300 mL) then filtered over celite. After separating the phase, the filter cake was washed with hexane (6×200 mL) which was subsequently used to extract the aqueous solution, then the aqueous solution was extracted with hexane (3×500 mL), the combined hexane was evaporated to get the crude product 16 g as an yellow oil which was redistilled under reduced pressure to afford the product 9.31 g (59.4%) at 140~142° C./1 mbar as a pale yellow liquid with purity 89.3%. The product contains 1.3% $Me_3$-TACN.

7 Preparation of $Ts_4$-DTNE in DMF

The mixture of $Ts_2$-TACN TsOH (3.0 g, 5 mmol) and $Na_2CO_3$ (2.12 g, 20 mmol) in 12 mL DMF was stirred at 110° C. for 5 min. Then 1,2-dibromoethane (0.43 mL, 5 mmol) was added and the resulting mixture was refluxed for 3 hrs (TLC showed the completion of the reaction, $CH_2Cl_2$/methanol (97:3)). After being cooled to room temperature, the mixture was poured into 200 mL water and was filtered. The solid was washed with water (4×50 mL), dried under vacuum to afford the product 1.8 g (82%) with 66% purity.

8 Preparation of $Ts_4$-DTNE in DMF/$H_2O$

The mixture of $Ts_2$-TACN TsOH (3.0 g, 5 mmol) in 24 mL DMF and $Na_2CO_3$ (2.12 g, 20 mmol) in 10 mL water was stirred at 110° C. for 5 min. Then 1,2-dibromoethane (0.43 mL, 5 mmol) was added and the resulting mixture was refluxed for 4 hrs (TLC showed the completion of the reaction, $CH_2Cl_2$/methanol (97:3)). After being cooled to room temperature, the mixture was poured into 200 mL water and was filtered. The solid was washed with water (4×50 mL), dried under vacuum to afford the product 1.76 g (80%) with 42% purity.

9 Preparation of $Ts_4$-DTNE in Toluene

The mixture of $Ts_2$-TACN TsOH (3.0 g, 5 mmol) and $Na_2CO_3$ (2.12 g, 20 mmol) in 20 mL toluene was stirred at 125° C. for 5 min. Then 1,2-dibromoethane (0.43 mL, 5 mmol) was added and the resulting mixture was refluxed for 6 hrs (TLC showed the completion of the reaction, $CH_2Cl_2$/methanol (97:3)). Then the solvent was evaporated and to the residue 50 mL water was added and the resulting mixture was filtered. The solid was washed with water (4×50 mL), dried under vacuum to afford the product 1.9 g (83%) with 56% purity.

10 Preparation of $Ts_4$-DTNE in Acetone

The mixture of $Ts_2$-TACN TsOH (3.0 g, 5 mmol) and $Na_2CO_3$ (2.12 g, 20 mmol) in 20 mL acetone was stirred at 85° C. for 5 min. Then 1,2-dibromoethane (0.43 mL, 5 mmol) was added and the resulting mixture was refluxed for 3 hrs (TLC showed the completion of the reaction, $CH_2Cl_2$/methanol (97:3)). Then the solvent was evaporated and to the residue 50 mL water was added and the resulting mixture was filtered. The solid was washed with water (4×50 mL), dried under vacuum to afford the product 1.95 g (89%) with 66% purity.

11. General Procedure for the Preparation of $[Mn_2(\mu\text{-}O)_2(\mu\text{-}CH_3COO)(Me_4\text{-}DTNE)]Cl_2$ Under $N_2$, to $Me_4$-DTNE in EtOH/$H_2O$(2:1, v/v), solid mixture of $MnCl_2 \cdot 4H_2O$ and sodium acetate were added. The mixture was stirred for 30 min at 58° C. After another stirring for 10 min cooled in an ice/water bath, the freshly prepared mixture of 1 M of $H_2O_2$ in water and 1.5 M of NaOH was added dropwise over 5 min. The mixture turned immediately dark green-brown. The mixture was stirred for 20 min in an ice water bath and then for 20 min at room temperature. 1 M of acetic acid was added. After stirring for another 20 min, the mixture was filtered to remove the brown solid and the filtering bed was washed with ethanol. Then the green filtrate was evaporated (the water bath temperature <45° C.). The residual dark green oil was co-evaporated with ethanol and ethyl acetate to facilitate the removal of most of the remaining water. Dark green oils were taken up in ethanol, and the insoluble white salts separated by filtration were washed with ethanol. After removing all ethanol, the dark green oil was obtained again. The small amount of ethanol was added and stirred for 2 min. Then the large amount of ethyl acetate was added. The green solid was precipitated immediately. After 3 hours at −20° C., the suspension was filtered off, with obtaining a green solid, which was washed with ethyl acetate, n-hexane, and dried under vacuum at 45° C. for 5 hrs to afford dark green powder as $[(Mn_2(\mu\text{-}O)_2(\mu\text{-}OAc)(Me_4\text{-}DTNE)]Cl_2 \cdot H_2O$.

11.1 Preparation of $[Mn_2(\mu\text{-}O)_2(\mu\text{-}CH_3COO)(Me_4\text{-}DTNE)]Cl_2$ from the Distilled $Me_4$-DTNE in the BuOH/$H_2O$ Route Distilled $Me_4$-DTNE obtained according to Example 6a (Example 11.1a) or 6c (Example 11.1b) (89.3% purity with 1.3% $Me_3$-TACN) (765 mg, 2 mmol); EtOH/$H_2O$ (2:1, v/v): 20 mL; $MnCl_2 \cdot 4H_2O$ (840 mg, 4.2 mmol); NaAc (82 mg, 1 mmol); 1 M of $H_2O_2$ in water (5 mL, 5 mmol); 1.5 M of NaOH (2.5 mL, 3.75 mmol); 1 M of HAc (1.25 mL, 1.25 mmol). 1.2 g of green powder as $[(Mn_2(\mu\text{-}O)_2(\mu\text{-}OAc)(Me_4\text{-}DTNE)]Cl_2 \cdot H_2O$.

UV-Vis purity of 91.1%, the yield of 86.8% (The yield (%)=the weight of the compound (g)×the purity of the compound (%)/the calcd. weight of the compound (g)). UV-Vis spectrum of a purified sample: ($\epsilon\square$: $mol^{-1} \cdot L \cdot cm^{-1}$, in water, Mw: 630): 271 nm (13332), 554 nm (317), 639 nm (327).

UPLC analysis confirmed 1.53% of the free $[H_2(Me_4\text{-}DTNE)]Cl_2$, 0.7% of the free $[H(Me_3\text{-}TACN)]Cl$, and 0.08% of $[(Mn_2(\mu\text{-}O)_3(Me_3\text{-}TACN)]Cl_2$.

Total chloride amount was 11.17%.

Water analysis (Karl-Fischer method): Anal. calcd. for $[(Mn_2(\mu\text{-}O)_2(\mu\text{-}OAc)(Me_4\text{-}DTNE)]Cl_2 \cdot H_2O$: 2.86%. Found: 1.14%.

11.2 Preparation of $[Mn_2(\mu\text{-}O)_2(\mu\text{-}CH_3COO)(Me_4\text{-}DTNE)]Cl_2$ from the Undistilled $Me_4$-DTNE in the BuOH/$H_2O$ Route Undistilled $Me_4$-DTNE obtained according to Example 6a (Example 11.2a) or 6b (Example 11.2b)(70.5% purity with 22.8% $Me_3$-TACN) (1.93 g, 4 mmol); EtOH/$H_2O$ (2:1, v/v): 40 mL; $MnCl_2 \cdot 4H_2O$ (2.22 g, 11.2 mmol); NaAc (166 mg, 2 mmol); 1 M of $H_2O_2$ in water (15 mL, 15 mmol); 1.5 M of NaOH (7.5 mL, 11.25 mmol); 1 M of HAc (2.5 mL, 2.5 mmol). 2.93 g of green powder as $[(Mn_2(\mu\text{-}O)_2(\mu\text{-}OAc)(Me_4\text{-}DTNE)]Cl_2 \cdot H_2O$. UV-Vis purity of 84.6%, the yield of 75.5%. (The yield (%)=the weight of the compound (g)×the purity of the compound ($)/(the calcd. weight of the compound (g)+the calcd. weight of $[(Mn_2(\mu\text{-}O)_3(Me_3\text{-}TACN)]Cl_2$ (g))).

UPLC analysis confirmed 6.96% of the free [H$_2$(Me$_4$-DTNE)]Cl$_2$, 3.2% of the free [H(Me$_3$-TACN)]Cl, and 4.3% of [(Mn$_2$(μ-O)$_3$(Me$_3$-TACN)]Cl$_2$.

Total chloride amount was 10.35%.

Water analysis (Karl-Fischer method): Anal. calcd. for [(Mn$_2$(μ-O)$_2$(μ-OAc)(Me$_4$-DTNE)]Cl$_2$·H$_2$O: 2.86%. Found: 1.07%.

11.3 Preparation of [Mn$_2$(μ-O)$_2$(μ-CH$_3$COO)(Me$_4$-DTNE)]Cl$_2$ from the Undistilled Me$_4$-DTNE in the CH$_3$CN/H$_2$O Route Undistilled Me$_4$-DTNE obtained according to Example 4a (Example 11.3a) or 4b (Example 11.3b)(84% purity with 5.2% Me$_3$-TACN): (1.62 g, 4 mmol); EtOH/H$_2$O (2:1, v/v): 40 mL; MnCl$_2$·4H$_2$O (1.78 g, 9 mmol); NaAc (166 mg, 2 mmol); 1 M of H$_2$O$_2$ in water (9 mL, 9 mmol); 1.5 M of NaOH (4.5 mL, 6.75 mmol); 1 M of HAc (2.5 mL, 2.5 mmol). 2.6 g of green powder as [(Mn$_2$(μ-O)$_2$(μ-OAc)(Me$_4$-DTNE)]Cl$_2$·H$_2$O.

UV-Vis purity of 84.8%, the yield of 88.7% (The yield (%)=the weight the compound (g)×the purity of the compound (%)/the calcd. weight of the compound (g)).

UPLC analysis confirmed 7.2% of the free [H$_2$(Me$_4$-DTNE)]Cl$_2$, 2.56% of the free [H(Me$_3$-TACN)]Cl, and 0.14% of [(Mn$_2$(μ-O)$_3$(Me$_3$-TACN)]Cl$_2$.

Total chloride amount was 10.91%.

Water analysis (Karl-Fischer method): Anal. calcd. for [(Mn$_2$(μ-O)$_2$(μ-OAc)(Me$_4$-DTNE)]Cl$_2$·H$_2$O: 2.86%. Found: 1.35%.

Using acetonitrile/H$_2$O as solvent for the formation of Ts$_4$-DTNE has advantages as the purity Me$_4$-DTNE product is much higher than when using other solvents. This leads to formation of Me$_4$-DTNE ligand that does not need to be further purified to make the dinuclear manganese complex. The method using butanol/water leads to a need to be distilled the Me$_4$-DTNE ligand to obtain high-purity material, leading to significant losses in yields. A yield improvement of the ligand of about 20% can be thus achieved (Experiment 4a vs experiment 6a or Experiment 4b vs Experiments 6b & 6c).

The invention claimed is:

1. A method of producing a compound of formula (A):

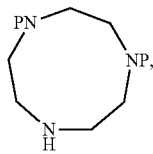

(A)

the method comprising the following step:
(a) reacting a compound of formula (B):

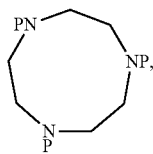

(B)

in an acidic medium comprising sulfuric acid, the molar ratio of the compound of formula (B) to sulfuric acid is in the range from 1:0.5 to 1:10, wherein P is an arylsulfonate protecting group; and (b) isolating the compound of formula (A) as a protonated salt in amorphous or crystalline form.

2. The method of claim 1, wherein the acidic medium further comprises an acid anhydride.

3. The method of claim 1, wherein the protonated salt has a counterion selected from the group consisting of: toluenesulfonic benzenesulfonic acid, sulfuric acid, acetic acid, formic acid, and propionic acid.

4. The method of claim 1, wherein the protonated salt is a salt of an aryl sulfonic acid.

5. The method of claim 3, wherein the protonated salt is the toluene sulfonic acid salt of 1,4-ditosyl-1,4,7-triazacyclononane.

6. The method of claim 1, wherein the step (a) is conducted at a reaction temperature from 100 to 160° C.

7. A method of producing a compound of formula (A):

(A)

the method comprising the following steps:
(a) reacting a compound of formula (B):

(B)

in an acidic medium comprising sulfuric acid, wherein P is an arylsulfonate protecting group, and (b) working up the reaction in step (a) when the conversion of the compound of formula (B) to the compound of formula (A) is at least 50 mol % yielding the compound of formula (A).

8. The method of claim 7, wherein the acidic medium further comprises an acid anhydride.

9. The method of claim 7, wherein step (a) is conducted at a reaction temperature from 100 to 160° C.

10. A method of producing a compound of formula (A):

(A)

the method comprising reacting a compound of formula (B):

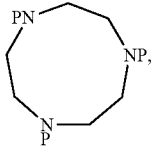
(B)

in an acidic medium comprising an acid anhydride, wherein P is arylsulfonate.

11. The method of claim 10, wherein the compound of formula (A) is isolated as a protonated salt of arylsulfonic acid HP, wherein P is the arylsulfonate from the compound of formula (B).

12. The method of claim 11, wherein the protonated salt is toluene sulfonic acid salt of 1,4-ditosyl-1,4,7-triazacyclononane.

13. A protonated salt of formula (A), having a counter ion HX, the protonated salt in amorphous or crystalline form:

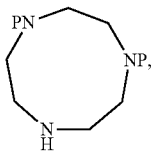
(A)

wherein P is a tosylate or benzene sulfonate; and HX is toluenesulfonic acid or benzenesulfonic acid.

14. The protonated salt of claim 13, which is (1,4-ditosyl-1,4,7-triazacyclonone) tosylate or (1,4-dibenzenesulfonyl-1,4,7-triazacyclonone)benzenesulfonate.

15. A method of producing a compound of formula (C):

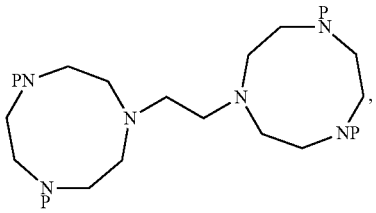
(C)

the method comprising the following step:
(a) reacting a compound of formula (A):

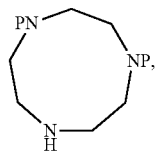
(A)

with a bridging element of the form $ZCH_2CH_2Z$, wherein P is an arylsulfonate protecting group and Z is a halogen selected from the group consisting of: Cl, Br, and I.

16. The method of claim 15, wherein the compound of formula (A) is reacted with the bridging element in a solvent selected from the group consisting of: acetonitrile, 1-butanol, 2-butanol, and t-butanol.

17. The method of claim 16, wherein the solvent is acetonitrile.

18. The method of claim 16, wherein the solvent comprises from 10 to 90 wt/wt % water.

19. The method of claim 17, wherein the acetonitrile comprises from 10 to 50 wt/wt % water.

20. A one-pot method for the preparation of 1,2-bis-(4,7-dimethyl-1,4,7-triazacyclonon-1-yl)-ethane ($Me_4$-DTNE), the method comprising
deprotecting a compound of formula (C):

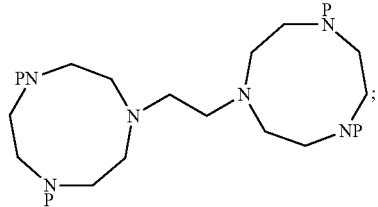
(C)

wherein P is arylsulfonate, with an acidic medium to form 1,2-bis(1,4,7-triazacyclonon-1-yl)-ethane; and
subsequently adding formaldehyde and formic acid to the acidic medium to form 1,2-bis-(4,7-dimethyl-1,4,7-triazacyclonon-1-yl)-ethane ($Me_4$-DTNE).

21. The one-pot method of claim 20, wherein P is tosylate.

22. The method of claim 1, wherein the reaction in step (a) is worked up when the conversion of the compound of formula (B) to the compound of formula (A) is at least 50 mol % yielding the compound of formula (A).

* * * * *